United States Patent
Kotulla

(10) Patent No.: US 10,227,973 B2
(45) Date of Patent: Mar. 12, 2019

(54) METHOD FOR CHECKING THE FUNCTIONALITY OF A METERING PUMP

(71) Applicant: Siemens Healthcare Diagnostics Products GmbH, Marburg (DE)

(72) Inventor: Guenther Kotulla, Frankfurt (DE)

(73) Assignee: Siemens Healthcare Diagnostics Products GmbH, Marburg (DE)

(*) Notice: Subject to any disclaimer, the term of this patent is extended or adjusted under 35 U.S.C. 154(b) by 122 days.

(21) Appl. No.: 15/405,222

(22) Filed: Jan. 12, 2017

(65) Prior Publication Data

US 2017/0204849 A1  Jul. 20, 2017

(30) Foreign Application Priority Data

Jan. 14, 2016 (EP) ..................... 16151198

(51) Int. Cl.
| | |
|---|---|
| *F04B 51/00* | (2006.01) |
| *B01L 3/02* | (2006.01) |
| *F04B 13/00* | (2006.01) |
| *F04B 49/06* | (2006.01) |
| *G01N 35/10* | (2006.01) |

(52) U.S. Cl.
CPC ............ *F04B 51/00* (2013.01); *B01L 3/0227* (2013.01); *F04B 13/00* (2013.01); *F04B 49/065* (2013.01); *G01N 35/1002* (2013.01); *B01L 2200/148* (2013.01); *F04B 2201/0201* (2013.01)

(58) Field of Classification Search
CPC ... F04B 51/00; A61M 5/16831; A61M 5/1456
See application file for complete search history.

(56) References Cited

U.S. PATENT DOCUMENTS

| 4,631,483 | A | * | 12/1986 | Proni | ................ | G01N 15/1209 |
| | | | | | | 141/67 |
| 4,796,787 | A | * | 1/1989 | Tsuyuki | .................... | B01J 4/02 |
| | | | | | | 137/121 |
| 5,529,754 | A | * | 6/1996 | Bonacina | ............... | G01B 7/023 |
| | | | | | | 324/519 |
| 9,675,756 | B2 | * | 6/2017 | Kamen | ............ | A61M 5/16859 |
| 2014/0058349 | A1 | * | 2/2014 | Bazargan | ........... | A61M 5/1456 |
| | | | | | | 604/500 |
| 2017/0204849 | A1 | * | 7/2017 | Kotulla | ................... | F04B 51/00 |

FOREIGN PATENT DOCUMENTS

| DE | 102006002763 A1 | 7/2007 |
| EP | 0681184 A1 | 11/1995 |
| WO | WO9214930 A1 | 9/1992 |
| WO | WO9608648 A1 | 3/1996 |

OTHER PUBLICATIONS

European Office Action and Search Report of European Application No. 16151198.5-1608 (2015P15214EP) dated Jun. 30, 2016.

* cited by examiner

*Primary Examiner* — Francis C Gray
(74) *Attorney, Agent, or Firm* — Dugan & Dugan, PC

(57) ABSTRACT

The invention relates to a metering pump, for example, for a pipetting apparatus in an automated analysis machine, and to a method for checking the functionality thereof.

12 Claims, 2 Drawing Sheets

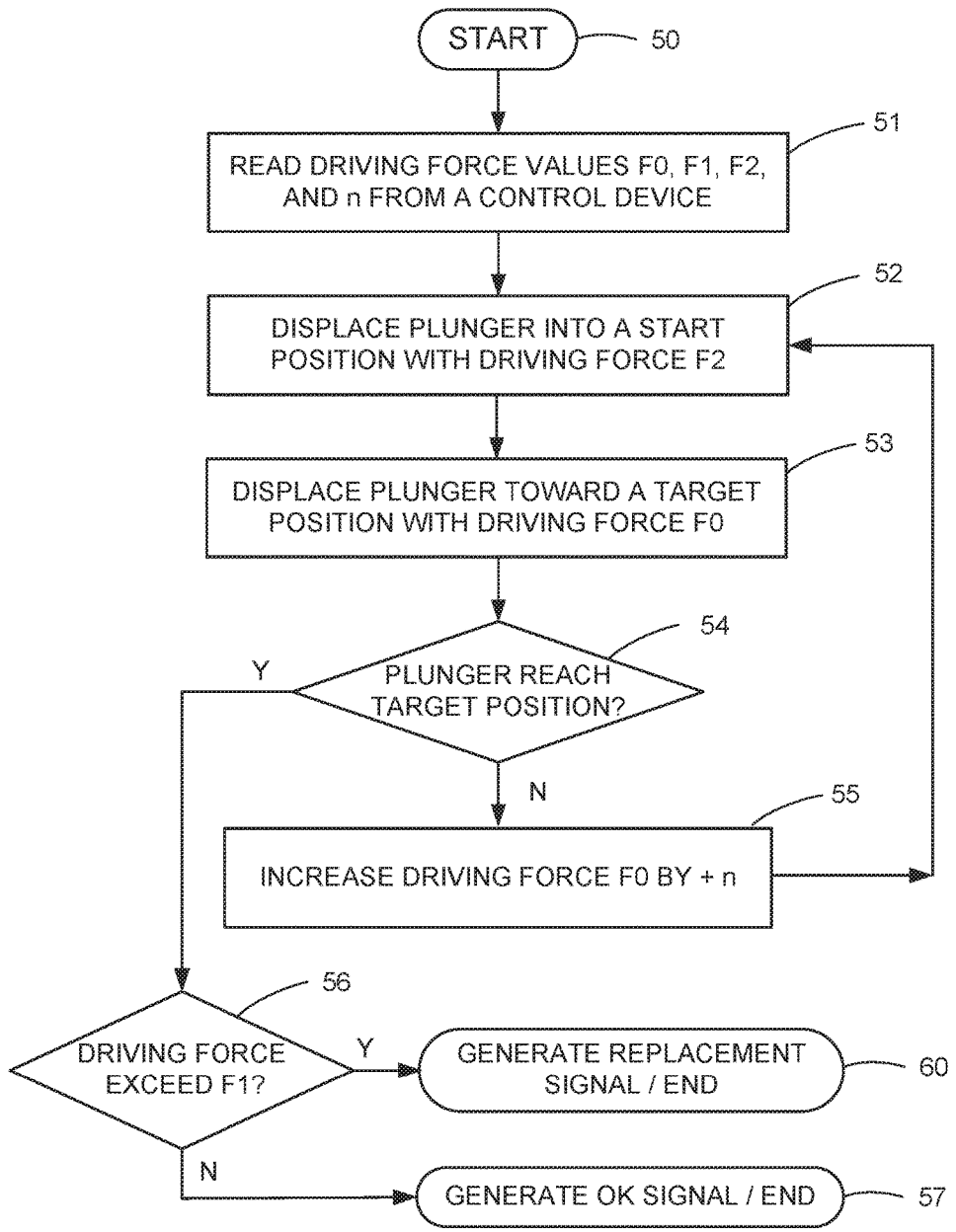

METHOD FOR CHECKING THE FUNCTIONALITY OF A METERING PUMP

CROSS REFERENCE TO RELATED APPLICATION

This claims priority to European Patent Application No. EP 16151198.5, filed Jan. 14, 2016, which is hereby incorporated by reference herein in its entirety for all purposes.

FIELD

The present invention lies in the field of automated analysis machines and relates to a metering pump, for example for a pipetting apparatus, and to a method for checking the functionality thereof.

BACKGROUND

Current analysis machines, as are used as a matter of routine in analytics, forensics, microbiology and clinical diagnostics, are able to carry out a multiplicity of detection reactions and analyses with a multiplicity of samples. In order to be able to carry out a multiplicity of examinations in an automated manner, various automatically operating apparatuses for the spatial transfer of measuring cells, reaction containers and reagent liquid containers are required, such as, e.g., transfer arms with a gripper function, transport belts or rotatable transport wheels, and apparatuses for transferring liquids, such as, e.g., pipetting apparatuses. The machines comprise a central control unit which, by means of appropriate software, is able to largely independently plan and work through the work steps for the desired analyses.

Many of the analysis methods used in such analysis machines operating in an automated manner are based on optical methods. Measurement systems based on photometric (e.g., turbidimetric, nephelometric, fluorometric or luminometric) or radiometric measurement principles are particularly widespread. These methods enable the qualitative and quantitative detection of analytes in liquid samples without having to provide additional separation steps. The determination of clinically relevant parameters, such as, e.g., the concentration or the activity of an analyte, is often implemented by virtue of an aliquot of a bodily fluid of a patient being mixed simultaneously or in succession with one or more test reagents in a reaction vessel, as a result of which a biochemical reaction is put into motion, which brings about a measurable change in an optical property of the test preparation.

The measurement result is, in turn, forwarded into a memory unit by the measurement system and evaluated. Subsequently, the analysis machine supplies a user with sample-specific measurement values by way of an output medium, such as, e.g., a monitor, a printer or a network connection.

Sample liquids or reagent liquids are usually transferred by means of automated pipetting apparatuses. Such pipetting apparatuses generally comprise a height-adjustable pipetting needle arranged vertically on a horizontally displaceable or swivelable transfer arm, which pipetting needle is connected to a pumping unit such that a desired volume of a liquid can be taken from a container by way of the pipetting needle, and output into a target container at a different location. Usually, the pipetting needle is displaced to a position over a liquid container with the aid of the transfer arm and then lowered into the liquid container and into the liquid contained therein. Once the desired volume has been withdrawn, the pipetting needle is driven upward and then driven to the desired target position over a liquid container, e.g., over a measurement cell, with the aid of the horizontally displaceable or swivelable transfer arm. There, the pipetting needle is lowered again, and the amount of liquid is output.

The pipetted liquid volumes lie in a range from approximately 5 to 500 microliters. Since pipetting errors or pipetting inaccuracies may lead to incorrect measurement results, very high requirements are placed on the pipetting accuracy. What is decisive here, inter alia, is the precision of the metering pump connected to the pipetting apparatus. The use of metering pumps in the form of reciprocating pumps, which are filled with a liquid or gaseous system medium and connected at the outlet opening thereof to the pipetting needle via a tubing system, is known. Negative pressure is generated by moving the pump plunger in order to suck liquid from a liquid container by means of the pipetting needle or positive pressure is generated in order to release the liquid again. Usually, such metering pumps are connected by way of a control line to a control device which, on the basis of specific control variables, is able to modify the plunger lift in accordance with the amount of volume to be pipetted.

It is problematic that a metering pump suffers from wear-and-tear over time, as result of which there are unwanted pipetting inaccuracies and, in the worst case, the abrupt outage of the metering pump and hence of the pipetting apparatus. Replacing a metering pump always requires the intervention of a user, usually even a specifically trained service technician. The unexpected outage of a metering pump, which reduces the throughput speed of the entire analysis machine and, in certain circumstances, causes a complete standstill of the analysis machine, should therefore be avoided where possible.

SUMMARY

Therefore, it would be desirable to be able to check, prior to the first activation of a metering pump, or else after a specific operating time, whether the metering pump is sufficiently functional for routine operation or whether the metering pump should be replaced.

The present invention is therefore based on the object of providing a method for checking the functionality of a metering pump, by means of which it is possible to determine whether the metering pump is sufficiently functional for routine operation or whether the metering pump should be replaced, with this determination being without intervention by a user, i.e., automatic.

The object is achieved by virtue of a check being carried out as to whether the driving force required to displace the plunger from a start position into a target position does not exceed a specific threshold.

The invention therefore relates to a method for checking the functionality of a metering pump comprising a cylinder and a motor-driven plunger which is movable in the cylinder, the plunger being displaceable between a start position and a target position. The method comprises the following steps:

a) displacing the plunger from the start position in the direction of the target position with a driving force F0 set in advance;

b) monitoring whether the plunger arrives at the target position;

c) returning the plunger to the start position with a driving force F2 set in advance, the driving force F0 being less than the driving force F2; and wherein d) a signal assigned to the metering pump is generated, the signal indicating the functionality of the metering pump—if it is determined that the plunger reaches the target position; and wherein e) the steps a) to c) are repeated with a driving force F0+n increased by a value n, the driving force F0+n being less than the driving force F2—if it is determined that the plunger does not reach the target position.

A "start position of the plunger" and a "target position of the plunger" should be understood to mean two different positions along the maximum linear travel of the plunger within the cylinder, with the target position being situated close to the outlet opening of the cylinder and—relative thereto—the start position being situated further away from the outlet opening of the cylinder. Both the start position and the target position may be fixed mechanically, for example, by a stop of the plunger at one end or the other end of the cylinder. Alternatively, the start position and/or the target position may also be set arbitrarily along the travel.

Preferably, the driving force F0, the driving force F2 and the value n, by means of which the driving force F0 may be increased a number of times, are set prior to activation of the metering pump.

Expediently, the driving force F2 is selected in such a way that it reliably ensures the displacement of the plunger from the target position back to the start position of the pump to be operated.

Then, the driving force F0 is selected in such a way that it is smaller than the driving force F2.

Preferably, the driving force F0 corresponds to about half the driving force F2.

The value n of a driving force, by means of which the driving force F0 may be increased a number of times, corresponds to a fraction of the driving force F0, for example, 10-30% of the driving force F0.

By way of example, monitoring as to whether the plunger reaches the target position may be carried out by virtue of a measurement being carried out with the aid of suitable sensors, e.g., an encoder on the stepper motor, as to whether the defined travel between start position and target position was in fact overcome, whether a defined number of steps could be carried out by the stepper motor, and the like.

If the method determines that the plunger already reaches the target position with the driving force F0, a signal assigned to the metering pump is generated, the signal indicating the functionality of the metering pump. Thereupon, the metering pump may be activated for the first time or continue to be operated without a restriction of the functionality being expected.

However, if it is determined that the plunger does not reach the target position, steps a) to c) are repeated with a driving force F0+n increased by the value n, the driving force F0+n always being less than the driving force F2. Steps a) to c) are repeated until either it is determined that the plunger reaches the target position and the driving force F0+xn required in this respect does not exceed a maximum driving force F1, which is set in advance and less than the driving force F2, or until it is determined that the plunger does not reach the target position with the maximum driving force F1 set in advance.

If it is then determined that the required driving force F0+xn does not exceed a maximum driving force F1 set in advance, a signal assigned to the metering pump indicating the functionality of the metering pump is generated. Thereupon, the metering pump may be activated for the first time or continue to be operated without a restriction of the functionality being expected.

By contrast, if it is determined that the plunger does not reach the target position with the maximum driving force F1 set in advance, a replacement signal assigned to the metering pump is generated. The replacement signal is directed to a user who can then undertake the replacement or servicing of the relevant metering pump in good time.

In a particularly preferred embodiment of the method according to the invention for operating a metering pump, the ratio of the driving force F2 and the driving force F0 or F0+xn is determined as a quality criterion for the power reserves of the metering pump. It was discovered that if the driving force F0 or F0+xn required for the plunger to reach the target position is more than 80% of the driving force F2, the risk of jamming is too high and the metering pump should therefore be replaced. Thus, preferably, a replacement signal assigned to the metering pump is generated if the driving force F0 or F0+xn required for the plunger to reach the target position is more than 80% of the driving force F2. In other words, the maximum driving force F1 set in advance is preferably 80% of the driving force F2.

Alternatively, it is possible to determine the quotient (Q1) of the driving force F2 and of the driving force F0 or F0+xn required for the plunger to reach the target position. If a quotient F2:F0 or F0+xn of less than 1.25 is obtained, a replacement signal assigned to the metering pump is generated.

In a further embodiment, the metering pump is additionally rendered inoperative if the plunger does not reach the target position with the maximum driving force F1 set in advance. This ensures that no potentially error-afflicted metering process or an uncontrollable pump outage as a result of jamming may occur.

A further subject matter of the present invention relates to a method for operating a metering pump, wherein the functionality of the metering pump is tested prior to activation of the metering pump by means of the method according to the invention described above and—if a signal assigned to the metering pump and indicating the functionality of the metering pump was generated—the plunger is moved from the start position in the direction of the target position and back again with the driving force F2 after activating the metering pump.

A further subject matter of the present invention is a metering pump comprising a cylinder, a plunger which is movable in the cylinder and a motor, wherein a driving force is transferable from the motor onto the plunger, as a result of which the plunger is displaceable between a start position and a target position. The metering pump further has a control device configured in such a way that it controls a method for operating the metering pump, the method comprising the following steps:

a) displacing the plunger from the start position in the direction of the target position with a driving force F0 set in advance;

b) monitoring whether the plunger arrives at the target position; and c) returning the plunger to the start position with a driving force F2 set in advance, the driving force F0 being less than the driving force F2; and wherein d) a signal assigned to the metering pump is generated, the signal indicating the functionality of the metering pump—if it is determined that the plunger reaches the target position; and wherein e) the steps a) to c) are repeated with a driving force F0+n increased by a value n, the driving force F0+n being less than the driving force F2—if it is determined that the plunger does not reach the target position.

The motor for driving the plunger may be an electric motor. Preferably, this is an electric stepper motor, particularly preferably a stepper motor with a sensor for reporting position (encoder) and a regulator. The stepper motor is operated with different current values for generating the driving forces F0, F0+n and F2.

In a preferred embodiment, the control device is further configured in such a way that it further controls that the steps a) to c) are repeated in step e) with a driving force F0+xn which is successively increased by a value xn, the driving force being less than the driving force F2, i) until it is determined that the plunger reaches the target position and the driving force F0+xn required in this respect does not exceed a maximum driving force F1, which is set in advance and less than the driving force F2, and, thereupon, a signal assigned to the metering pump indicating the functionality of the metering pump is generated; or ii) until it is determined that the plunger does not reach the target position with the maximum driving force F1 set in advance and, thereupon, a replacement signal assigned to the metering pump is generated.

Furthermore, the control device may additionally be configured in such a way that it further controls that the metering pump is rendered inoperative if the plunger does not reach the target position with the maximum driving force F1 set in advance.

Preferably, the control device of the metering pump according to the invention comprises a memory unit in which the driving force F2 set in advance, the driving force F0 set in advance, the value n for increasing the driving force F0 and/or the maximum driving force F1 set in advance are stored. The phrase "set in advance" means that the characteristics were ascertained by suitable test series prior to activation of the metering pump.

A further subject matter of the present invention relates to an automated analysis machine comprising at least one pipetting apparatus which comprises a metering pump according to the invention. The analysis machine may comprise a plurality of such pipetting apparatuses, for example, a first pipetting apparatus for transferring sample liquids, such as, e.g., blood, plasma, serum, urine, liquor, etc., and a second pipetting apparatus for transferring reagent liquids, for example, buffers, antibody solutions, antigen solutions, etc.

The pipetting apparatuses may be fastened to horizontally displaceable or swivelable transfer arms which are automatically movable. A pipetting apparatus comprises a hollow needle, by means of which a liquid volume to be transferred may be sucked in and released again at a different location. To this end, the pipetting needle is connected to a metering pump according to the invention by way of a tube system.

Preferably, the automated analysis machine furthermore comprises an output medium which converts the signal indicating the functionality of the metering pump generated by the control device of the metering pump and/or the replacement signal into a signal that is perceivable visually and/or acoustically and indicates the latter. By way of example, the output medium may be a screen, a warning lamp or loudspeaker and convert the replacement signal generated by the control device of the metering pump into a signal that is perceivable visually and/or acoustically and indicate the latter. By way of example, the replacement signal may be indicated in the form of a text message or in the form of a pictogram on a screen of the automated analysis machine or it may be output in the form of an acoustic signal by a loudspeaker of the automated analysis machine or it may be output in the form of a visual signal by a warning lamp of the automated analysis machine.

Below, the invention is explained on the basis of a drawing.

BRIEF DESCRIPTION OF THE DRAWINGS

FIG. 3 shows a flowchart of a method for checking the functionality of a metering pump.

The same parts are provided with the same reference signs in all the figures.

DETAILED DESCRIPTION

Figure 1:
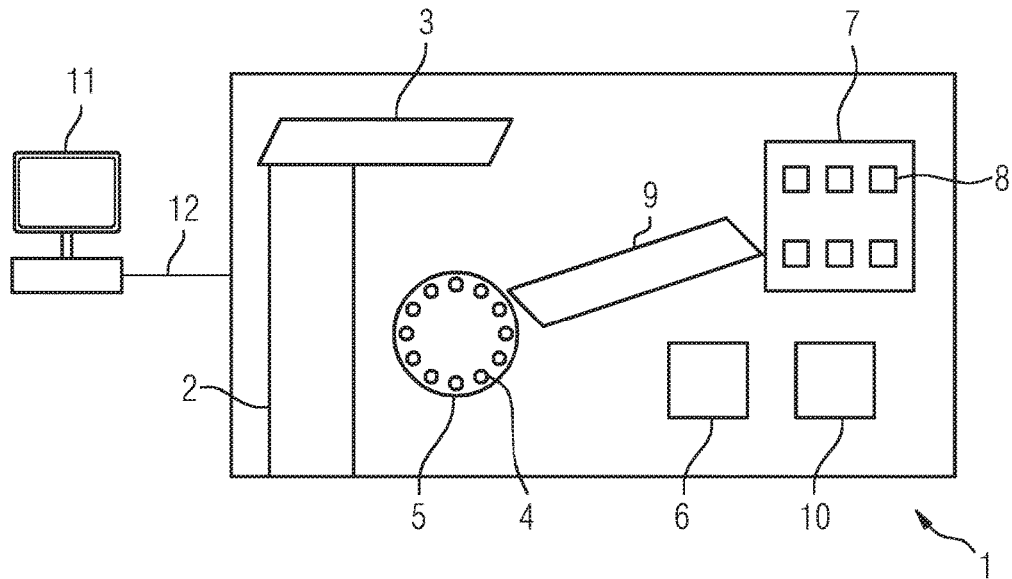
FIG. 1 shows an automated analysis machine according to the invention.

FIG. 1 is a schematic illustration of an automated analysis machine 1 with some of the components contained therein. Here, only the most important components are depicted in a very simplified manner in order to explain the basic functionality of the automated analysis machine 1 without, in the process, representing the individual parts of each component in detail.

The automated analysis device 1 is embodied to fully automatically carry out very different analyses of blood or other bodily fluids without any activities of a user being required in this respect. Instead, necessary interventions of a user are restricted to servicing or repairing functional units and to refilling work, for example, if cuvettes need to be refilled or liquid containers need to be replaced.

The patient samples are fed to the automated analysis machine 1 on carriages (not depicted in any more detail) by way of a supply rail 2. By way of example, information in respect of the analyses to be carried out for each sample may be transferred by means of barcodes applied to the sample vessels, the barcodes being read in the automated analysis machine 1. By means of a pipetting needle, sample aliquots are taken from the sample vessels with the aid of a first pipetting apparatus 3.

The sample aliquots are likewise fed to cuvettes (not depicted in any more detail) which are arranged in receiving positions 4 along a rotatable incubation device 5 which is temperature controlled to be at 37° C. The cuvettes are removed from a cuvette storage container 6. Reagent vessels 8 with various reagent liquids are stored in the reagent vessel storage container 7, which is cooled to approximately 8-10° C. Reagent liquid is removed from a reagent vessel 8 by means of the pipetting needle of a second pipetting apparatus 9 and released for providing a reaction mix in a cuvette in a receiving position 4. After the incubation time, the cuvette with the reaction mix is transported by a transfer arm with a gripper (not depicted here) from the incubation device 5 to a photometric measuring unit 10, where the absorbance of the initial reaction solution is measured.

The whole process is controlled by a central control unit 11, such as, e.g., a computer connected by a data line 12, assisted by a plurality of further electronic circuits and microprocessors (not depicted here in any more detail) within the automated analysis machine 1 and the components thereof.

Figure 2:
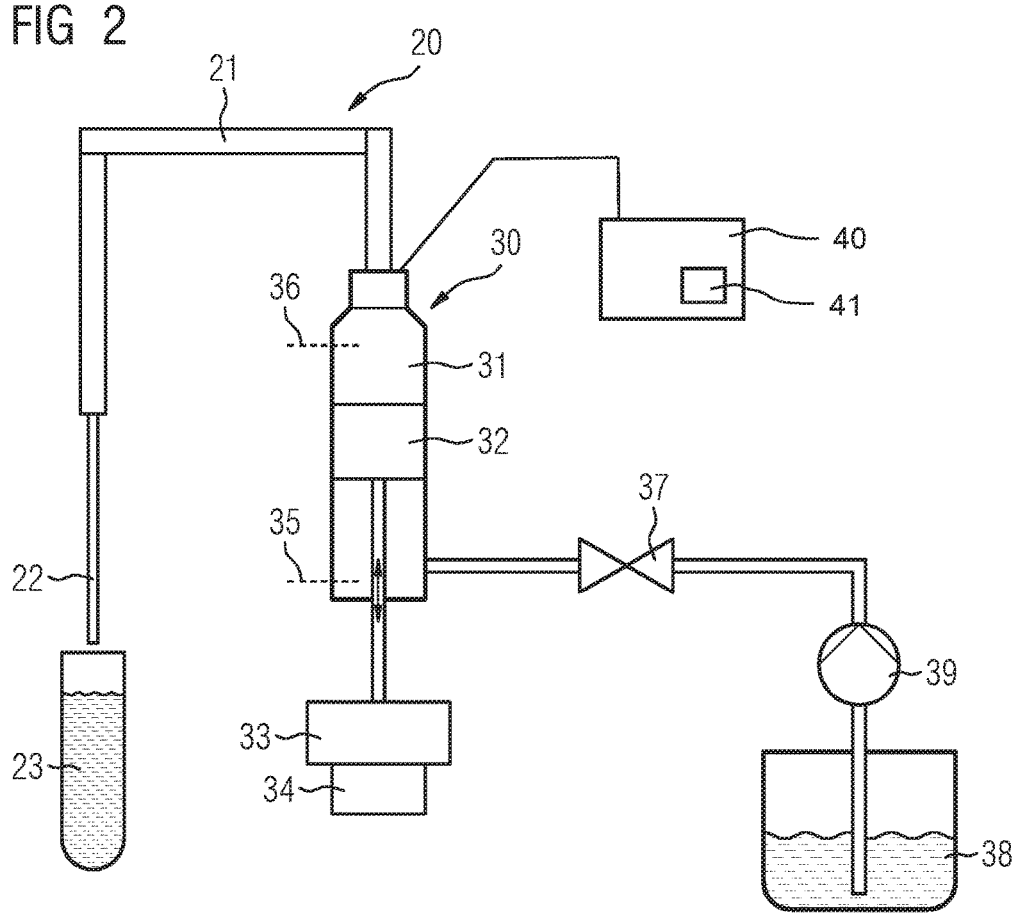
FIG. 2 shows a pipetting apparatus comprising a metering pump according to the invention.

FIG. 2 is a schematic illustration of a pipetting apparatus 20 comprising a metering pump 30 according to the invention. The pipetting apparatus 20 comprises a height adjustable pipetting needle 22 fastened to a horizontally displaceable transfer arm 21, by means of which pipetting needle liquid may be taken from a liquid vessel 23 or released into a liquid vessel 23. The metering pump 30 comprises a cylinder 31 and a plunger 32 which is linearly displaceable within the cylinder 31. The volume of the cylinder 31 is 500 microliters. The plunger 32 is coupled to a stepper motor 33, which comprises an encoder 34 as a sensor for reporting the position. The stepper motor 33 may be operated with different current strengths, and so differently strong driving forces may be exerted on the plunger 32. For the purposes of checking the functionality of the metering pump 30, which is explained in more detail with reference to FIG. 3, the plunger 32 is displaced with defined driving forces between the start position 35, set in advance, at −600 steps and the target position 36, set in advance, at −800 steps. During routine operation of the pipetting apparatus 20, defined liquid volumes are taken up or released by the pipetting needle 22 as a result of moving the plunger 32 when the valve 37 is closed. If the valve 37 is open, a cleaning solution 38, such as, e.g., deionized water or a disinfection solution, may be pumped through the metering pump 30 and the pipetting needle 22 by means of a pumping apparatus 39 for cleaning purposes.

FIG. 3 illustrates a flowchart of a method for checking the functionality of the metering pump 30 of the pipetting apparatus 20 from FIG. 2, the latter being part of an automated analysis machine 1. In step 50, a start signal for carrying out the method for checking the functionality of the metering pump 30 is output by the central control unit 11 of the automated analysis machine 1. Thereupon, in step 51, the values, set in advance, for the driving force F2 (600 mA stepper motor current), the driving force F0 (300 mA stepper motor current), the value n for increasing the driving force F0 (90 mA) and the maximum driving force F1 (80% of F2, i.e., 480 mA stepper motor current) are initially read from the control device 40 of the metering pump 30, the values being stored in a configuration file in the control device 40, and the plunger 32 is displaced into the start position 35 with the driving force F2 in step 52. Subsequently, in step 53, the plunger 32 is displaced with the driving force F0 in the direction of the target position 36. Step 54 monitors whether the plunger 32 has reached the target position 36 with the applied driving force (F0). If this is the case, a signal assigned to the metering pump 30 indicating the functionality of the metering pump 30 is generated in step 57 and the process is terminated. By contrast, if step 54 determines that the plunger 32 has not reached the target position 36 with the applied driving force (F0), the driving force F0 is increased by the value n (90 mA) in step 55 and steps 52, 53 and 54 are repeated with a driving force F0+xn increased step-by-step until the plunger 32 has reached the target position 36. Then, step 56 monitors whether the driving force F0+xn (300 mA+x*90 mA) does not exceed the maximum driving force F1 (480 mA). If it is determined that the driving force F0+xn, with which the target position 36 was reached, has not exceeded F1, a signal assigned to the metering pump 30 indicating the functionality of the metering pump 30 is generated in step 57 and the process is terminated. By contrast, if it is determined that the driving force F0+xn, with which the target position 36 was reached, has exceeded F1, a replacement signal assigned to the metering pump 30 is generated in step 60, the replacement signal indicating the lacking functionality of the metering device 30, and the process is terminated.

LIST OF REFERENCE SIGNS

1 Analysis machine
2 Supply rail
3 Pipetting apparatus
4 Receiving position
5 Incubation device
6 Cuvette storage container
7 Reagent vessel storage container
8 Reagent vessel
9 Pipetting apparatus
10 Measuring unit
11 Central control unit
12 Data line
20 Pipetting apparatus
21 Transfer arm
22 Pipetting needle
23 Liquid vessel
30 Metering pump
31 Cylinder
32 Plunger
33 Stepper motor
34 Encoder
35 Start position
36 Target position
37 Valve
38 Cleaning solution
39 Pumping apparatus
40 Control device
41 Memory unit
50-60 Method steps

What is claimed is:

1. A method for checking the functionality of a metering pump comprising a cylinder and a motor-driven plunger which is movable in the cylinder, the plunger being displaceable between a start position and a target position, the method comprising the following steps:
   (a) displacing the plunger via a motor from the start position in a direction of the target position with a driving force F0, wherein an initial value of the driving force F0 is stored in a control device and is less than a driving force F2, a value of the driving force F2 stored in the control device;
   (b) monitoring via a sensor whether the plunger arrives at the target position; and
   (c) returning the plunger via the motor to the start position with the driving force F2; wherein:
   (d) a signal is generated by the control device indicating the functionality of the metering pump if it is determined that the plunger reaches the target position and the driving force F0 is less than a maximum driving force F1, a value of the maximum driving force F1 stored in the control device; and
   (e) the steps a) to c) are repeated with the driving force F0 increased by a value n resulting in a driving force F0+n, the value n stored in the control device, the driving force F0+n being less than the driving force F2, if it is determined that the plunger does not reach the target position.

2. The method as claimed in claim 1, wherein the steps a) to c) are repeated in step e) with the driving force F0 successively increased by the value n resulting in a driving force F0+xn, where x is the number of times step e) is repeated, the driving force F0+xn being less than the driving force F2,
   (i) until it is determined via the sensor that the plunger reaches the target position and the driving force F0+xn does not exceed the maximum driving force F1, which is less than the driving force F2, wherein a signal indicating the functionality of the metering pump is generated by the control device; or (ii) until it is determined that the plunger reaches the target position with the driving force F0+xn exceeding the maximum driving force F1, wherein a replacement signal is generated by the control device.

3. The method as claimed in claim 2, wherein the metering pump is rendered inoperative if the plunger does not reach the target position with the driving force F0+xn equal to or exceeding the maximum driving force F1.

4. The method as claimed in claim 2, wherein the maximum driving force F1 is 80% of the driving force F2.

5. The method as claimed in claim 1, wherein the driving force F0 corresponds to approximately half of the driving force F2.

6. A method for operating a metering pump, wherein the functionality of the metering pump is tested prior to activation of the metering pump by the method as claimed in claim 1 and—if a signal indicating the functionality of the metering pump was generated—the method comprises moving the plunger via the motor from the start position in the direction of the target position and back again with the driving force F2 after activating the metering pump.

7. A metering pump comprising a cylinder, a plunger which is movable in the cylinder, and a motor, wherein a driving force is transferable from the motor onto the plunger, as a result of which the plunger is displaceable between a start position and a target position, and wherein the metering pump has a control device configured such that it controls a method for checking the functionality of the metering pump, the method comprising:
  (a) displacing the plunger via a motor from the start position in a direction of the target position with a driving force F0, wherein an initial value of driving force F0 is stored in the control device and is less than a driving force F2, a value of the driving force F2 stored in the control device;
  (b) monitoring via a sensor whether the plunger arrives at the target position; and
  (c) returning the plunger via the motor to the start position with the driving force F2; wherein:
  (d) a signal is generated by the control device indicating the functionality of the metering pump if it is determined that the plunger reaches the target position and the driving force F0 is less than a maximum driving force F1, a value of the maximum driving force F1 stored in the control device; and
  (e) the steps a) to c) are repeated with the driving force F0 increased by a value n resulting in a driving force F0+n, the value n stored in the control device, the driving force F0+n being less than the driving force F2, if it is determined that the plunger does not reach the target position.

8. The metering pump as claimed in claim 7, wherein the control device is further configured such that it further controls that the steps a) to c) are repeated in step e) with the driving force F0 successively increased by the value n resulting in a driving force F0+xn, where x is the number of times step e) is repeated, the driving force F0+xn being less than the driving force F2,
  (i) until it is determined via the sensor that the plunger reaches the target position and the driving force F0+xn does not exceed the maximum driving force F1, which is less than the driving force F2, wherein a signal indicating the functionality of the metering pump is generated by the control device; or
  (ii) until it is determined that the plunger reaches the target position with the driving force F0+xn exceeding the maximum driving force F1 wherein a replacement signal is generated by the control device.

9. The metering pump as claimed in claim 8, wherein the control device is further configured such that it further controls that the metering pump is rendered inoperative if the plunger reaches the target position with the driving force F0+xn exceeding the maximum driving force F1.

10. The metering pump as claimed in claim 8, wherein the control device comprises a memory unit in which the value for the driving force F2, the initial value for the driving force F0, the value n for increasing the driving force F0 and the value for the maximum driving force F1 are stored.

11. An automated analysis machine comprising at least one pipetting apparatus which comprises a metering pump as claimed in claim 7.

12. The automated analysis machine as claimed in claim 11 and further comprising an output medium, wherein the output medium converts the signal indicating the functionality of the metering pump generated by the control device of the metering pump or the replacement signal into a signal that is perceivable visually or acoustically and indicates the latter.

* * * * *